(12) United States Patent
Clubb et al.

(10) Patent No.: US 6,203,732 B1
(45) Date of Patent: Mar. 20, 2001

(54) METHOD FOR MANUFACTURING INTRALUMINAL DEVICE

(75) Inventors: Elizabeth A. Clubb; Thomas L. Clubb, both of Hudson, WI (US); James V. Donadio, III, Chaska, MN (US)

(73) Assignee: Intra Therapeutics, Inc., St. Paul, MN (US)

( * ) Notice: Subject to any disclaimer, the term of this patent is extended or adjusted under 35 U.S.C. 154(b) by 0 days.

(21) Appl. No.: 09/109,554

(22) Filed: Jul. 2, 1998

(51) Int. Cl.[7] .............................. B29C 33/42; B32B 1/08
(52) U.S. Cl. ............................. 264/81; 264/219; 264/313; 264/317; 164/464; 164/465; 216/8; 216/9; 216/10; 430/320; 430/323; 205/67; 205/74; 623/1
(58) Field of Search .............................. 264/81, 219, 317, 264/313; 164/465, 464; 216/8–10; 430/320, 323; 205/74, 67; 623/1

(56) References Cited

U.S. PATENT DOCUMENTS

| | | |
|---|---|---|
| 4,955,899 | * 9/1990 | Della Corna et al. ................ 623/1 |
| 5,421,955 | 6/1995 | Lau et al. ................................ 216/48 |
| 5,573,520 | 11/1996 | Schwartz et al. . |
| 5,741,429 | 4/1998 | Donadio, III et al. .................. 216/8 |
| 5,772,864 | * 6/1998 | Moller et al. ........................... 205/73 |
| 5,907,893 | * 6/1999 | Zadno-Azizi et al. .................. 29/6.1 |
| 6,019,784 | * 2/2000 | Hines ....................................... 623/1 |

FOREIGN PATENT DOCUMENTS 2219408   10/1998  (CA) .

* cited by examiner

*Primary Examiner*—Jill L. Heitbrink
*Assistant Examiner*—Suzanne E. McDowell
(74) *Attorney, Agent, or Firm*—Merchant & Gould P.C.

(57) ABSTRACT

A generally tubular device (e.g., a stent or catheter) for placement in a lumen of a patient's body is made by forming a depressed pattern in an external surface of a mold. The depressed pattern corresponds to a desired shape of the generally tubular device. A material is deposited in the depressed pattern for the material to form the generally tubular device conforming to the depressed pattern. The generally tubular device is separated from the mold.

12 Claims, 2 Drawing Sheets

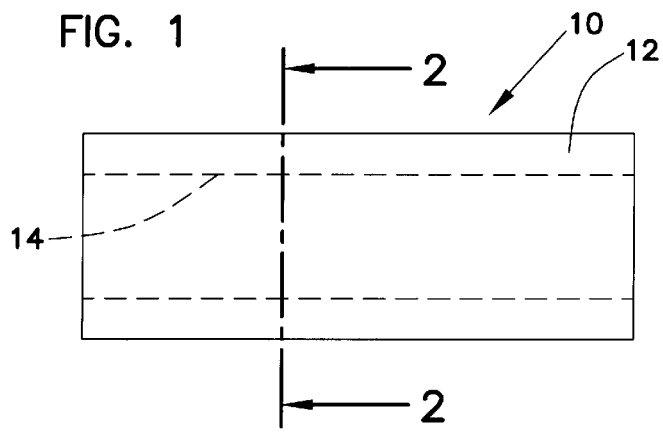 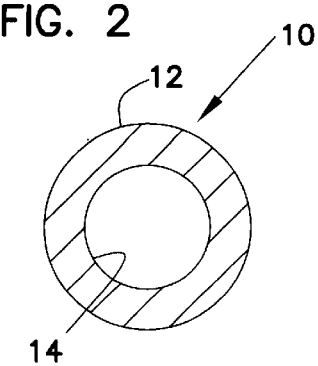 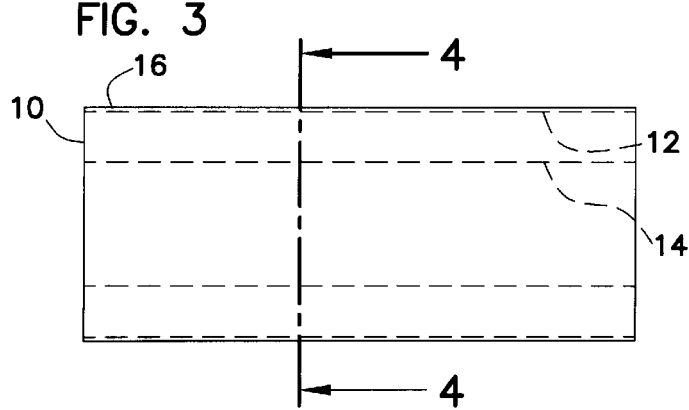 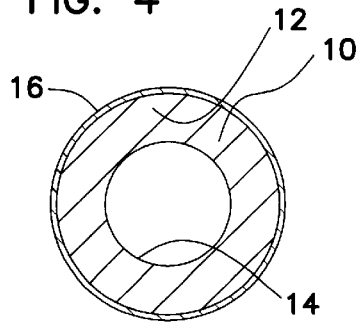 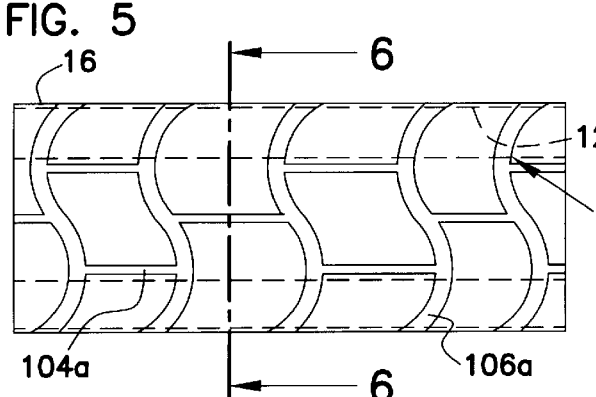 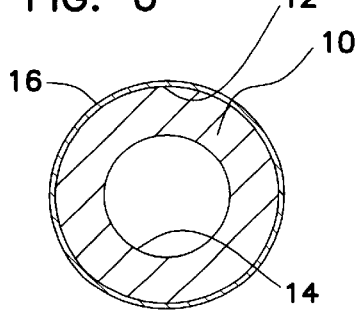 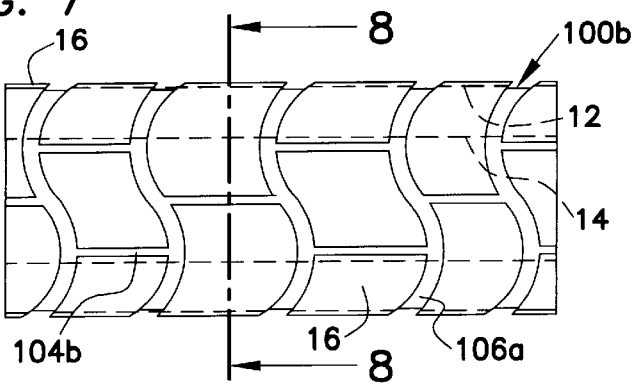 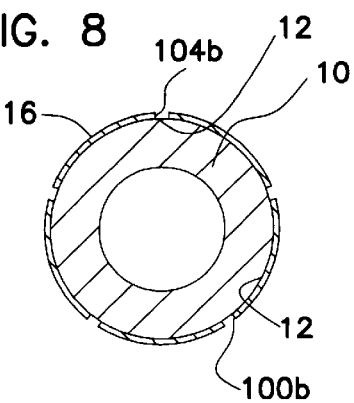

METHOD FOR MANUFACTURING INTRALUMINAL DEVICE

BACKGROUND OF THE INVENTION

1. Field of the Invention

This invention pertains to tubular intraluminal devices (such as stents or catheters) for placement in a lumen of a patient's body. More particularly, this invention pertains to a method for manufacturing such devices.

2. Description of the Prior Art

Intraluminal devices for placement in a lumen of a patient are widely used. For example, stents are commonly used to treat obstructed coronary arteries. Typically, such stents are reticulated tubular structures. The stents are placed on a balloon tip catheter and advanced through the patient's blood vessels to an occluded artery. At the occluded site, the balloon is expanded to enlarge the stent's diameter. With the stent so enlarged, the balloon is deflated and the catheter is removed from the patient leaving the enlarged stent in place with the intent that the formerly occluded site is held patent by the stent.

In addition to advancing stents as described above, catheters are used in a wide variety of applications. Accordingly, catheters are available in a wide variety of designs. Many such designs require extremely small diameter and flexible catheters. For example, in neurological applications, catheters must be extremely narrow and flexible in order to be advanced through the patient's vasculature to a desired site.

To achieve the small diameters and desired flexibility as well as other properties, stent, catheters and other tubular intraluminal devices may include hollow tubes fabricated with a plurality of openings formed through the walls of the tube. For example, U.S. Pat. No. 5,573,520 dated Nov. 12, 1996 teaches a catheter with a tube having a plurality of apertures to increase flexibility.

Since intraluminal devices have such small diameters, it is extremely difficult to fabricate these devices. For example, prior art stents would be formed by laser-machining a solid-walled metal tube. Through accurate control of the laser, the laser would be axially and circumferentially moved relative to the stent and selectively energized to form highly detailed holes through the wall of the tube and, hence, form a stent of desired intricate lattice pattern.

Laser machining is very costly as well as presenting other problems. As a result, the art has developed other techniques for forming reticulated intraluminal devices. For example, U.S. Pat. No. 5,421,955 to Lau et al. dated Jun. 6, 1995 describes a process for forming stents from a hollow metal tube. The tube is coated with a coating resistant to chemical etching. Using a laser, portions of the coating are removed to expose a pattern on the tube corresponding with a pattern of tube material to be removed in a desired stent design. With the coating so removed, the tube is chemically etched to remove tube material exposed by reason of the selective removal of the coating. Subsequent to such etching, the remainder of the coating is removed to finish the stent forming process. Even though the laser is not being used to remove metal, the use of a laser is still required to remove the coating. Such a use is complicated, costly and difficult to control.

Commonly assigned U.S. Pat. No. 5,741,429 issued Apr. 20, 1998 permits the formation of reticulated intraluminal tubular devices such as stents and catheters in a chemical etching process not requiring the use of lasers and their disadvantages. In this patent, a chemical resistant coating is applied to a tube. Using a photo-mask, portions of the coating are exposed to a light source. The exposed portions are removed in a developing process to expose a pattern on the surface of the tube. The tube is then chemically etched to remove tube material exposed through the developed pattern. Following such etching, the remainder of the coating is removed.

While the '429 patent represents a significant advance in the production of stents and catheters, chemical etching presents certain challenges. For example, when a chemical etchant is applied to a limited exposed area on the exterior of a tube, the etchant does not dissolve perfectly radially toward the center of the tube. This tendency precludes certain stent pattern geometries which can be formed in a chemical etching process. For example, intricate, narrow corners are difficult to form in stents and catheters made by chemical etching. Further, the non-radial etching path can result in the formation of stent or catheter walls being non-radial relative to the tube's axis. These non-radial walls intersect with the interior cylindrical surface of the stent tube in such a manner that sharp knife edges can be formed. Such edges are undesirable and require further process.

II. SUMMARY OF THE INVENTION

According to a preferred embodiment of the present invention, a method is disclosed for forming a generally tubular device (e.g., a stent or catheter) for placement in a lumen of a patient's body. The method includes forming a depressed pattern in an external surface of a mold. The depressed pattern corresponds to a desired shape of a generally tubular device for placement in a lumen of a patient's body. A material is deposited in the depressed pattern for the material to form the generally tubular device conforming to the depressed pattern. The generally tubular device is separated from the mold.

III. BRIEF DESCRIPTION OF THE DRAWINGS

FIG. 1 is a side-elevation view of a blank mandrel for use in the method of the present invention;

FIG. 2 is a view taken along line 2—2 in FIG. 1;

FIG. 3 is a side-elevation view of the mandrel of FIG. 1 coated with a photoresist;

FIG. 4 is a view taken along line 4—4 in FIG. 3;

FIG. 5 is a side-elevation view of the photoresist-coated mandrel of FIG. 3 following light imaging for imaging a desired device pattern onto the photoresist;

FIG. 6 is a view taken along line 6—6 in FIG. 5;

FIG. 7 is a side-elevation view of the imaged mandrel of FIG. 5 with the imaged pattern developed and removed;

FIG. 8 is a view taken along line 8—8 of FIG. 7;

IV. DESCRIPTION OF THE PREFERRED EMBODIMENT

Referring now to the several drawing figures in which identical elements are numbered identically throughout, a description of a preferred embodiment will now be provided. In providing such a description, specific processes will be described. It will be appreciated that variants (some of which will be later described) of such specifics are intended to be included within the scope of the appended claims.

Figure 17:
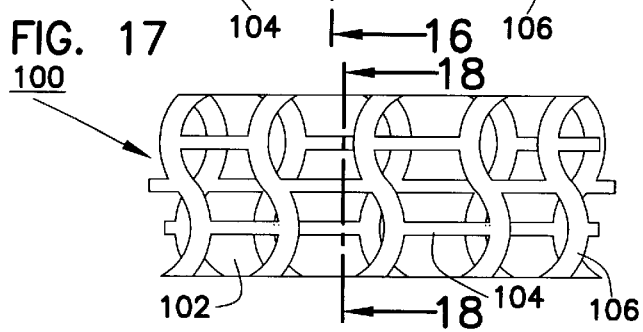
FIG. 17 is a side-elevation view of a finished intraluminal device fabricated following removal of the mandrel material from the ground mandrel of FIG. 15.
Figure 18:
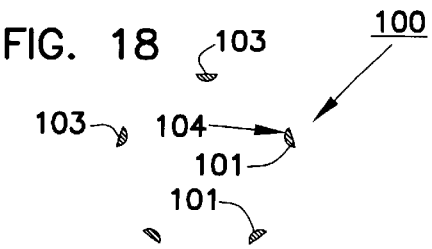
FIG. 18 is a view taken along line 18—18 of FIG. 17.

Referring to FIGS. 1–2, a metal tube 10 is shown for use as a mandrel in forming a tubular intraluminal device according to the present invention. For ease of illustration, the present invention will be described for making a stent 100 (shown in FIGS. 17–18) but is also applicable to the manufacture of other tubular intraluminal devices (e.g., catheters).

By way of example, the stent 100 is a reticulated tube of about 0.050 inch (about 1.25 mm) outside diameter, 0.75 inch (about 19 mm) length and 0.005 inch (about 0.13 mm) wall thickness. It will be appreciated the recitation of such dimensions is a non-limiting example and is given to demonstrate the extremely small tubular structures to which this invention applies. In the example, the stent 100 is titanium and has a reticulated structure with a plurality of openings 102 defined by axial and circumferential portions 104, 106. For such a titanium stent 100, the mandrel material is stainless steel which may be dissolved by an etchant which does not dissolve titanium. Again, the recitation of such materials is non-limiting and is given to illustrate the present invention.

The mandrel 10 has a length at least as long as the desired length of the stent 100 and has an outside diameter of about 0.050 inch (about 1.25 mm) approximately equal to the outside diameter of the stent 100. As will become apparent with reference to FIGS. 15–16, the outside diameter of mandrel 10 could be greater than the stent 100. The excess diameter can then be removed in a grinding process or other metal removing process as discussed with reference to FIGS. 15–16. In the embodiments shown, the mandrel 10 is shown as a hollow tube (with a wall thickness of about 0.010 inch or about 0.25 mm) but could be a solid rod.

As will be described, the present invention forms a depressed pattern 100c in the exterior cylindrical surface 12 of the mandrel 10. The depressed pattern 100c has axial and circumferential portions 104c, 106c corresponding to and matching the desired stent pattern 100 (and portions 104, 106). The stent material is deposited into the depressed pattern 100c to assume the desired stent pattern 100. The stent 100 so-formed is separated from the mandrel 10.

The depressed pattern 100c is formed in the outer cylindrical surface 12 of the mandrel 10. The depressed pattern 100c does not penetrate through the interior cylindrical surface 14 of the mandrel 10.

In the presently preferred embodiment, the depressed pattern 100c is formed in a photo-etching process similar to that described in the aforementioned, commonly assigned U.S. Pat. No. 5,741,429. Specifically, a photo-resist coating 16 (by way of example, about 0.0003 inch or about 0.008 mm thick) is placed on the outer cylindrical surface 12 of the mandrel 10 (see FIGS. 3–4). The coating 16 is resistant to chemical etching.

Using a photo-imaging process as described in U.S. Pat. No. 5,741,429 (incorporated herein by reference), the coating 16 is exposed to a light source (not shown) through a photo-mask (not shown) having a light transparent pattern corresponding to the desired stent pattern 100. The light photo-sensitizes a pattern 100a on the coating 16. As an alternative, the pattern 100a could be laser printed. The photo-sensitized pattern 100a has axial and circumferential portions 104a, 106a corresponding to and matching the desired stent pattern 100. (see FIGS. 5–6).

The sensitized pattern 100a is then removed in a developing process (again as disclosed in U.S. Pat. No. 5,741,429). The developing process exposes a pattern 100b on the surface 12 of the mandrel 10. The exposed surface pattern 100b has axial and circumferential portions 104b, 106b corresponding to and matching the desired stent pattern 100 (FIGS. 7–8).

Figure 9:
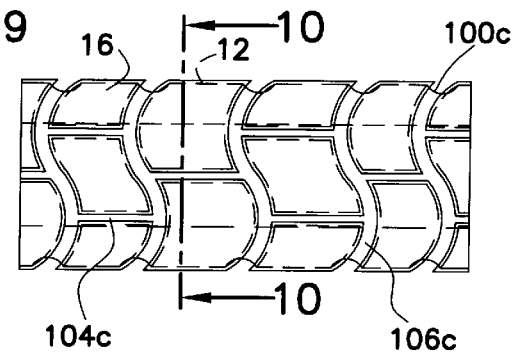
FIG. 9 is a side-elevation view of the developed mandrel of FIG. 8 following etching of the portions of the mandrel exposed through the developed pattern.
Figure 10:
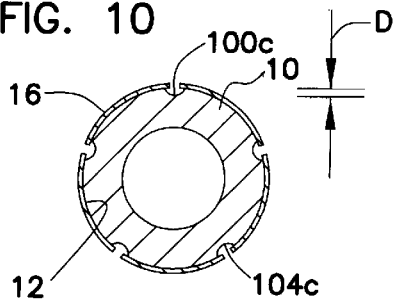
FIG. 10 is a view taken along line 10—10 of FIG. 9.

With a surface pattern 100b on the mandrel 10 so exposed and with the remainder of the mandrel surface 12 protected by the undeveloped coating 16, the mandrel 10 is etched with an etching solution (again, as disclosed in U.S. Pat. No. 5,741,429) to form the depressed pattern 100c. Unlike U.S. Pat. No. 5,741,429, the etching process is not continued until the etchant dissolves completely though the thickness of the mandrel 10. Instead, the etching process is controlled (as is well within the skill of the art) to terminate the etching after the etching has penetrated a desired depth D (FIG. 10) into the mandrel 10 without penetrating through the interior surface 14 of the mandrel 10. The desired depth D is selected to approximate the desired wall thickness of the stent 10. As previously discussed, excess thickness can be removed through a grinding or other metal removing process as will be described with reference to FIGS. 15–16.

Figure 11:
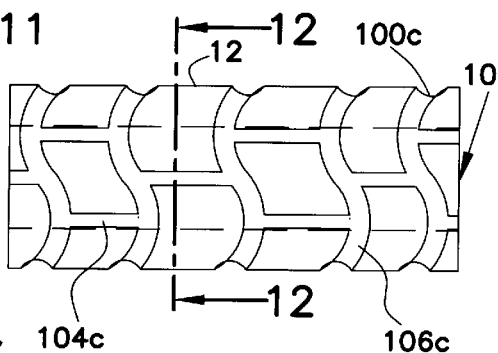
FIG. 11 is a side-elevation view of the etched mandrel of FIG. 9 with undeveloped photoresist stripped away.
Figure 12:
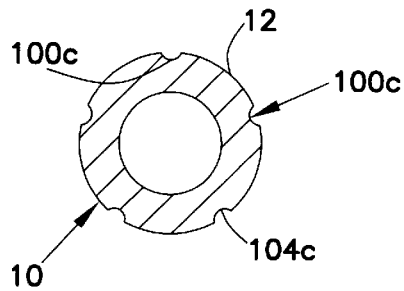
FIG. 12 is a view taken along line 12—12 of FIG. 11.
Figure 13:
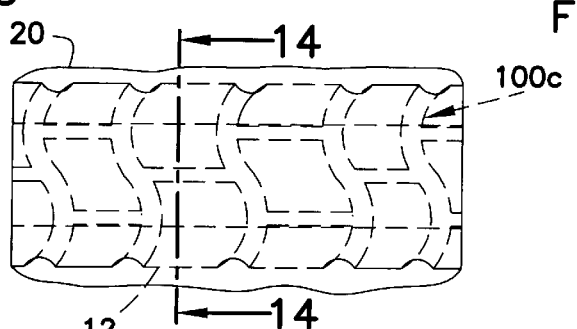
FIG. 13 is a side-elevation view of the stripped mandrel of FIG. 11 following deposit of a metal layer.
Figure 14:
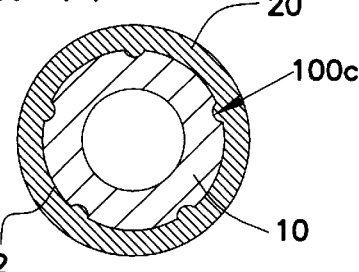
FIG. 14 is a view taken along line 14—14 of FIG. 13.

After the depressed pattern 100c is etched into the mandrel 10, the remaining, unexposed area of coating 16 is removed (FIGS. 11–12). The stent material is applied to the mandrel outer surface 12 and into the depressed pattern 100c in any one of a number of suitable ways. For example, the titanium may be vapor deposited onto the mandrel 10 in a titanium layer 20. The stent material 20 then fills the depressed pattern 100c and coats the remaining outer surface 12 of the mandrel 10.

Figure 15:
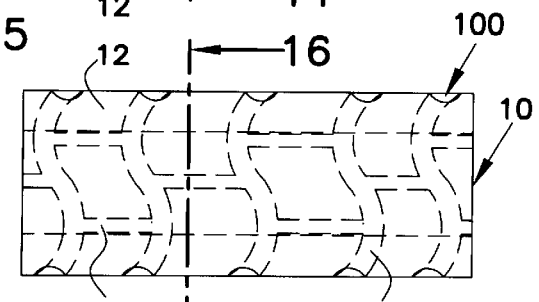
FIG. 15 is a side-elevation view of the deposited mandrel of FIG. 13 with excess deposited metal ground away.
Figure 16:
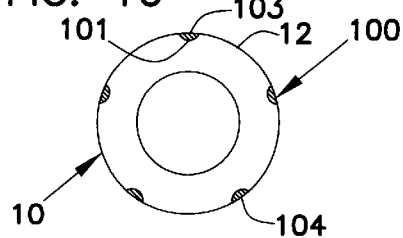
FIG. 16 is a view taken along line 16—16 of FIG. 15.

Since the stent material 20 outside of the depressed pattern 100c is undesired, such excess material is removed. By way of example, the excess material may be machined or ground off in a center grinding process. FIGS. 15–16 illustrate the mandrel 10 and stent material 100 following such grinding. The only stent material on the mandrel is the stent material 100 in the depressed pattern 100c. The stent material includes axial and circumferential portions 104, 106 filling and conforming to the axial and circumferential portions 104c, 106c of the depressed pattern.

The stent material 100 is then separated from the mandrel 10 to yield the finished stent 100. Such removal may include dissolving the mandrel 10 in a solvent which dissolves the mandrel material but not the stent material. It will be appreciated that selection of materials and solvents and etchants for selectively dissolving one material without substantial dissolving another is well within the ordinary skill of the art.

With reference to FIG. 12, the depressed pattern 100c has a concave cross-section and is rounded at the bottom 101c. This is attributable to the non-radial dissolving mentioned previously with reference to the prior art. However, in the present invention, this does not result in sharp edges at the interior surface of the stent 100 as in the prior art. Instead, the depressed pattern 100c is a mold and the resulting bottom surface 101 of the stent 100 is rounded and convex. As a result, intricate patterns not previously possible with the prior art are possible with the present invention. Further, sharp edges are avoided on the interior surface 101 of the stent. Also, while the interior surface 101 of the stent 100 is rounded and free of sharp edges (which is desirable with balloon catheters), the outer surface 103 of the stent 100 is cylindrical conforming to the interior surface of the lumen.

Many other advantages are attained by the present invention. For example, through multiple masking and etching processes, a depressed pattern of varying depths can be formed. Such a depressed pattern will form a stent with structural members of varying thickness. This will give stent designers added freedom when designing stents, catheters and other intraluminal devices with enhanced properties. Also, multiple layers of materials can be placed in the depressed pattern. For example, a radiopaque layer may be vacuum deposited between two layers of other materials selected for better tissue or blood compatibility.

A wide variety of materials can be used with the present invention. By way of non-limiting example, the stent material can be tantalum, niobium, zirconium, titanium or platinum vapor applied on a stainless steel mandrel. Also, the stent could be molten stainless steel cast onto a molybdenum or tungsten mold. The foregoing examples are non-limiting and are given solely to illustrate the numerous permutations of alternatives for materials and processes in keeping with the teachings of the present invention.

While the mandrel's depressed pattern has been described in a preferred embodiment as being chemically milled (as described in U.S. Pat. No. 5,741,429), the depressed pattern could be formed in any suitable manner including laser milling, EDM (electro-discharge machining), cast or machined. Likewise, the stent material can be deposited in the depressed pattern in any one of a number of suitable ways. Without limitation, these include:

1. casting the stent material as a molten material poured into the depressed area and retained by an outer casing;
2. electro-forming;
3. forge or crimped (i.e., an outer tube of stent material is placed surrounding the mandrel and forcibly urged into the depressed area);
4. sputter deposition;
5. ion plating; and
6. placement as a powder metal later sintered.

From the foregoing, it has been shown how the present invention has been attained in a preferred embodiment. Modifications and equivalents of the disclosed concepts, such as those which are apparent to one skilled in the art, are intended to be included within the scope of the appended claims.

What is claimed is:

1. A method for forming a generally tubular device for placement in a lumen of a patient's body, the method comprising:
    (a) coating an external surface of a mold with a coating;
    (b) removing a portion of the coating to form a pattern corresponding to a desired shape of the generally tubular device for placement in a lumen of a patient's body;
    (c) forming a depressed pattern in the external surface of the mold with the depressed pattern corresponding to the pattern in the coating and the desired shape of the generally tubular device for placement in a lumen of a patient's body;
    (d) depositing a material in the depressed pattern for the material to form the generally tubular device conforming with the depressed pattern; and
    (e) separating the generally tubular device from the mold.

2. A method according to claim 1 wherein the step of separating the generally tubular device from the mold comprises:
    (a) separating the generally tubular device from the mold by chemically etching the mold while leaving the tubular device substantially unetched.

3. A method according to claim 1 wherein the step of coating an external surface of a mold with a coating comprises:
    (a) coating an external surface of a substantially cylindrical mold with the coating.

4. A method according to claim 3 wherein the step of forming a depressed pattern in an external surface of the mold comprises:
    (a) forming a depressed pattern in an external surface of the substantially cylindrical mold, the depressed pattern surrounding a cylindrical axis of the mold.

5. A method according to claim 4 wherein the step of forming a depressed pattern in an external surface of the substantially cylindrical mold comprises:
    (a) chemically etching the depressed pattern into the external surface of the substantially cylindrical mold.

6. A method according to claim 1 wherein after the step of forming a depressed pattern in the external surface of the mold and before the step of depositing a material in the depressed pattern, removing the coating from the external surface to expose an undepressed remainder.

7. A method according to claim 6 wherein the step of depositing a material in the depressed pattern comprises:
    (a) depositing a material in the depressed pattern and at least partially on the undepressed remainder.

8. The method according to claim 7, further comprising:
    (a) removing the material from the undepressed remainder.

9. A method according to claim 5 comprising:
    (a) applying a photo-resist coating to the external surface of the mold;
    (b) photo-imaging a pattern corresponding to the depressed pattern onto the photo-resist coating;
    (c) developing the photo-resist coating to remove the pattern and expose the external surface of the mold corresponding to the depressed pattern; and
    (d) chemically etching the mold to remove mold material exposed by the pattern and form the depressed pattern.

10. A method according to claim 1 wherein the step of depositing a material comprises:
    (a) vapor depositing of the material.

11. A method according to claim 1 wherein the step of depositing a material comprises:
    (a) flowing the material in a molten state into the depressed pattern.

12. A method according to claim 1 wherein the step of depositing a material comprises:
    (a) surrounding the external surface of the mold with a tube of the material; and
    (b) urging the material radially inwardly into the depressed pattern.

* * * * *